Aug. 12, 1969 F. C. BOYD, JR Plant Pat. 2,916
DOGWOOD TREE
Filed Oct. 25, 1967
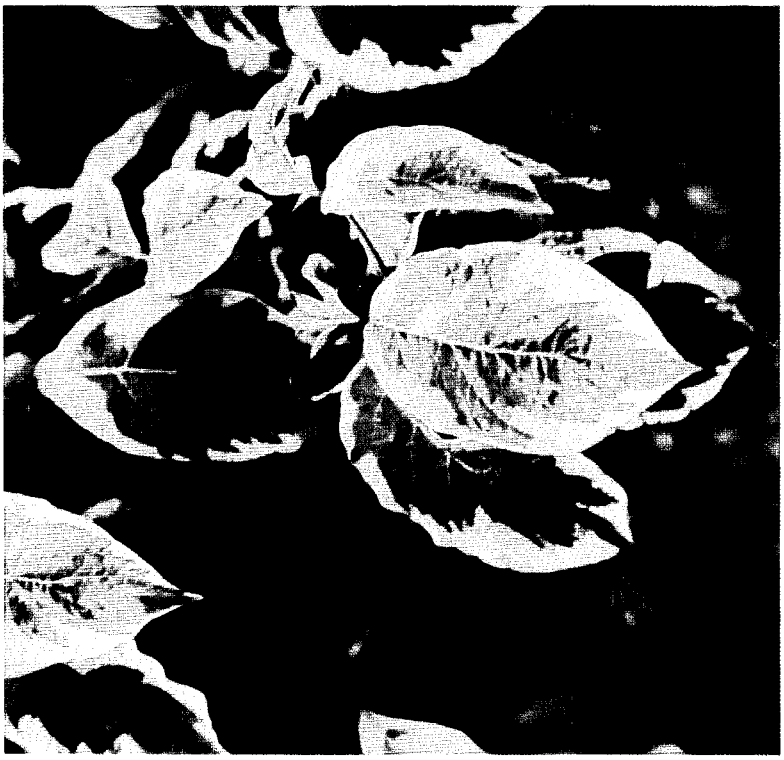
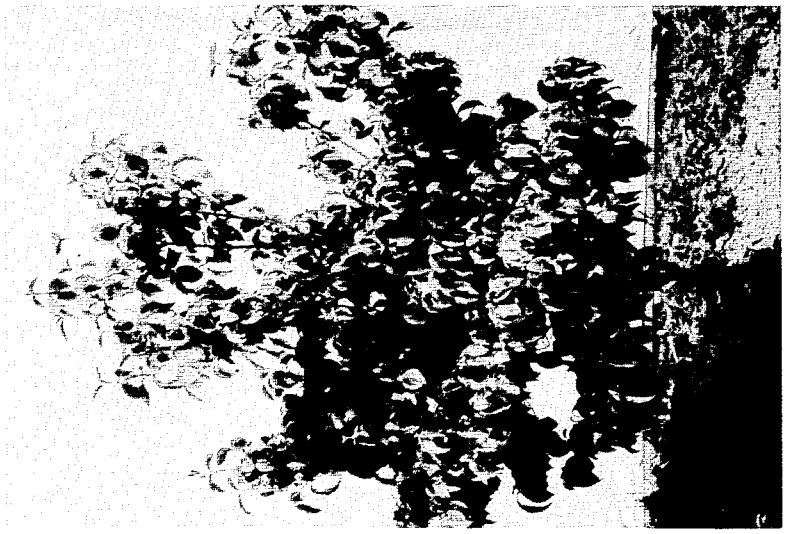
Inventor.
F. C. Boyd, Jr.
By: Robb & Robb
Attorneys.

United States Patent Office

Plant Pat. 2,916
Patented Aug. 12, 1969

2,916
DOGWOOD TREE

Fernando C. Boyd, Jr., McMinnville, Tenn., assignor to Boyd Nursery Company, Inc., McMinnville, Tenn., a corporation of Tennessee Filed Oct. 25, 1967, Ser. No. 678,120
Int. Cl. A01h 5/02
U.S. Cl. Plt.—51 1 Claim The present invention relates to a new and distinct variety of dogwood tree which was discovered by me on the cultivated nursery property of my assignee near McMinnville, Tenn., as a newly found seedling of unknown parentage, but apparently being a mutation of an unidentified variety of the dogwood species botanically known as *Cornus florida.*

At the time of my discovery, a block of some 100,000 dogwood seedlings of the species *Cornus florida* were being grown in the nursery aforesaid under my direction and supervision, preparatory to being budded. In the course of my work, my attention was attracted to one particular plant in the seedling block which appeared to be significantly different from all other plants in this block, due to its unusual leaf color which was dark green in the central area of the leaf and yellow around the leaf edge. I thereupon took steps to carefully preserve and observe this seedling and to asexually reproduce the same, as performed in our nursery by buddings, and over succeeding years, continued budding the same until a substantial number of budded plants were developed, although the original plant from which the buds were first taken did not survive. Continued and prolonged observations and tests of the budded plants showed that the unusual and distinctive leaf coloration comes true and is established and transmitted through succeeding propagations, and have convinced me that the new seedling is definitely distinguished from its parent, as well as from all other dogwood varieties of which I am aware, as evidenced by the following unique combination of characteristics which are outstanding therein:

(1) A rapid, upright growing habit;

(2) A distinctive and attractive leaf coloration ranging from Moderate Yellow-Green to Strong Yellow-Green over an irregular central area, with the surrounding leaf margin being Vivid Yellow in a border of irregular width and suffused irregularly along the leaf veins towards and into the central area of the leaf;

(3) Constant retention of the leaf color throughout the growing season from early spring to late fall when the green color becomes an attractive maroon color, and the yellow color becomes suffused with pink; and (4) The ability to grow in full sun without losing or diminishing the striking foliage colors.

To the best of my knowledge, the only dogwood varieties which approach the distinctiveness of my new variety are *Cornus florida* "Welchii" (unpatented), which has variegated leaves of green, creamy-white and pink colors, and which is a slow grower which does not do well when grown in full sun so far as the variegated foliage effect is concerned, and the *Cornus florida* variety "Rainbow" (Plant Patent No. 2743), which has variegated foliage of green and yellow colors which changes color throughout the growing season, with the green color becoming greenish-purple and other areas becoming red, yellowish or tan, contrary to the new variety which remains relatively constant from the first appearance of the leaves in the spring, without appreciable change until late fall (usually in the month of October in Tennessee).

The accompanying drawing shows a typical tree of my new dogwood variety, as well as typical leaf specimens illustrated on a somewhat enlarged scale, as depicted in color as nearly true as it is reasonably possible to make the same in a color illustration of this character.

The following is a detailed description of the foliage of my new variety, with color terminology in accordance with the Nickerson Color Fan, published by Munsell Color Company, Inc., of Baltimore, Md., except where general color terms of ordinary dictionary significance are obvious, and it being understood that except for the foliage, the plant and flowers of the new variety generally correspond to and are typical of the species *Cornus florida*:

Leaves: From medium quantity to dense.

*Size.*—Length—from 2.1 inches to 4.9 inches, averaging 4.13 inches±0.45 inch. Width (at widest point)—from 1.2 inches to 3.1 inches, averaging 2.43 inches±0.43 inch.

*Color.*—Irregular central area ranges from Moderate Yellow-Green, Hue 5GY 5/6 to Strong Yellow-Green, Hue 5GY 6/8, and is surrounded at leaf margin by border of irregular width of Vivid Yellow, Hue 5Y 8/12, which is suffused along leaf veins towards and into green center of leaf, these colors remaining constant throughout the growing season until late fall when the green colors turn an attractive maroon and the yellow color becomes suffused with pink; the amount of yellow coloration is directly related to the amount of exposure to sunlight, with little or no yellow color appearing in heavily shaded leaves.

*General color tonality.*—Brilliant green and gold.

I claim:

1. A new and distinct variety of dogwood tree, substantially as herein shown and described, characterized particularly as to novelty by a general similarity of the plant and flowers, except for its foliage, to the species botanically known as *Cornus florida*, but being distinguished from all other varieties of the aforesaid species by the unique combination of a rapid, upright growing habit, a distinctive and attractive leaf coloration ranging from Moderate Yellow-Green to Strong Yellow-Green over an irregular central area, with the surrounding leaf margin being Vivid Yellow in a border of irregular width and suffused irregularly along the leaf veins towards and into the central area of the leaf, constant retention of the leaf color throughout the growing season from early spring to late fall when the green color becomes an attractive maroon color, and the yellow color becomes suffused with pink, and the ability to grow in full sun without losing or diminishing the striking foliage colors.

No references cited.

ROBERT E. BAGWILL, Primary Examiner